US011273097B2

(12) United States Patent
Cheng et al.

(10) Patent No.: US 11,273,097 B2
(45) Date of Patent: Mar. 15, 2022

(54) INDUCTIVE THERAPEUTICAL INSTRUMENT GENERATING ELECTRIC CURRENT AND SKIN CARE METHOD

(71) Applicant: Guangzhou Mozhen Electronic Technology Co., LTD., Guangdong (CN)

(72) Inventors: Lizhi Cheng, Guangzhou (CN); Guifang Huang, Guangzhou (CN)

(73) Assignee: Guangzhou Mozhen Electronic Technology Co., LTD., Guangdong (CN)

( * ) Notice: Subject to any disclaimer, the term of this patent is extended or adjusted under 35 U.S.C. 154(b) by 351 days.

(21) Appl. No.: 16/408,280

(22) Filed: May 9, 2019

(65) Prior Publication Data
US 2019/0343712 A1  Nov. 14, 2019

(30) Foreign Application Priority Data

May 10, 2018 (CN) .......................... 201810453404.4

(51) Int. Cl.
*A61H 15/00* (2006.01)
*A61H 23/02* (2006.01)

(52) U.S. Cl.
CPC ......... *A61H 15/0078* (2013.01); *A61H 23/02* (2013.01)

(58) Field of Classification Search
CPC .... A61H 15/0078; A61H 15/02; A61H 23/02; A61H 23/0263; A61H 2201/5028;
(Continued)

(56) References Cited

U.S. PATENT DOCUMENTS 7,891,037 B2 * 2/2011 Richmond ............ A61H 7/005
15/97.1
8,500,355 B2 * 8/2013 Liu .................... A61H 23/0263
401/209
(Continued)

FOREIGN PATENT DOCUMENTS

CN   103505253   1/2014
CN   205698457   11/2016
(Continued)

OTHER PUBLICATIONS

Chinese First Office Action, dated Jan. 4, 2019, in Chinese Patent Application No. CN2018104534044 (filed May 10, 2018), parent of the present application, 11 pp. (with English translation).
(Continued)

*Primary Examiner* — Justine R Yu
*Assistant Examiner* — Kelsey E Baller
(74) *Attorney, Agent, or Firm* — Leydig, Voit & Mayer, Ltd.

(57) ABSTRACT

Provided is an inductive therapeutical instrument generating electric current and a skin care method, which relates to the field of skin care apparatuses. The above inductive therapeutical instrument is mainly used for applying a material body to the skin and massaging and maintaining the skin. The inductive therapeutical instrument mainly includes a material storage container and a massage head. The material body is stored in the material storage container, and the material body is squeezed into the massage head by squeezing the material storage container, and is applied to the skin through a material discharging hole on the massage head. Moreover, during use, the inductive therapeutical instrument can generate a microcurrent that acts on the skin so as to improve the skin condition.

12 Claims, 4 Drawing Sheets

(58) Field of Classification Search
CPC ...... A61H 2201/105; A61H 2201/1207; A61H 2201/1654; A61H 2201/169; A61H 2201/5005; A61H 7/005; A61N 1/328; A61M 37/00; A61M 2037/0007
USPC .................. 601/19; 401/209; 222/196–203, 222/206–215
See application file for complete search history.

(56) References Cited

U.S. PATENT DOCUMENTS

| | | | | |
|---|---|---|---|---|
| 9,872,813 | B2* | 1/2018 | Giraud | A61H 15/02 |
| 10,463,531 | B2* | 11/2019 | Brunson | A61N 1/303 |
| 2002/0158089 | A1* | 10/2002 | Mehta | B65D 1/323 |
| | | | | 222/420 |
| 2004/0068213 | A1* | 4/2004 | Fujisawa | A61H 23/0263 |
| | | | | 601/70 |
| 2005/0027217 | A1* | 2/2005 | Tsai | A61H 7/003 |
| | | | | 601/17 |
| 2006/0276730 | A1* | 12/2006 | Thiebaut | A61H 7/003 |
| | | | | 601/112 |
| 2011/0091264 | A1* | 4/2011 | Zhang | A45D 34/04 |
| | | | | 401/139 |
| 2011/0091265 | A1* | 4/2011 | Zhang | A61H 7/005 |
| | | | | 401/195 |
| 2011/0095052 | A1* | 4/2011 | Zhang | A45D 34/00 |
| | | | | 222/94 |
| 2014/0288469 | A1* | 9/2014 | Wang | A61H 23/0263 |
| | | | | 601/46 |
| 2015/0073438 | A1* | 3/2015 | Levy | A45D 44/22 |
| | | | | 606/131 |

FOREIGN PATENT DOCUMENTS

| | | |
|---|---|---|
| CN | 106963617 | 7/2017 |
| CN | 206350811 | 7/2017 |

OTHER PUBLICATIONS

Chinese Search Report, undated, in Chinese Patent Application No. CN2018104534044 (filed May 10, 2018), parent of the present application, 1 p.
Chinese Second Office Action, dated Apr. 19, 2019, in Chinese Patent Application No. CN2018104534044 (filed May 10, 2018), parent of the present application, 6 pp.
Chinese Supplemental Search Report, undated, in Chinese Patent Application No. CN2018104534044 (filed May 10, 2018), parent of the present application, 2 pp.

* cited by examiner

INDUCTIVE THERAPEUTICAL INSTRUMENT GENERATING ELECTRIC CURRENT AND SKIN CARE METHOD

CROSS-REFERENCE TO RELATED APPLICATIONS

The present disclosure claims the priority of the Chinese patent application No. 201810453404.4, filed with the Chinese Patent Office on May 10, 2018 and entitled "Inductive Therapeutical Instrument Generating Electric Current and Skin Care Method", which is incorporated herein by reference in its entirety.

TECHNICAL FIELD

The present disclosure relates to the field of skin care apparatuses, and particularly to an inductive therapeutical instrument generating electric current and a skin care method.

BACKGROUND OF THE INVENTION

With the improvement of living standards, people raise increasingly higher requirements on skin care. Researchers in the field of skin care apparatuses have also developed numerous skin care apparatuses, but the skin care effects of the skin care apparatuses in the prior art still need to be improved.

BRIEF SUMMARY OF THE INVENTION

The present disclosure is implemented as follows:

an inductive therapeutical instrument generating electric current, comprising:

a material storage container, configured to store a material body, the material storage container being compressible;

a massage head, which is of a hollow structure and made of an electrically conductive material, the massage head comprising a massage surface, provided thereon with a material discharging hole; the massage head being connected with the material storage container, and the material body capable of flowing through an interior of the massage head and flowing out from the material discharging hole;

a vibration motor, provided in the massage head; and a touch piece and a power supply, the touch piece being made of an electrically conductive material, the touch piece, the vibration motor and the massage head being connected in series, and the massage head, the touch piece and the power supply being connectable by an electrically conductive element to form a closed loop circuit.

A skin care method, using the inductive therapeutical instrument generating electric current and comprising the steps of:

a. hand-holding the inductive therapeutical instrument generating electric current, and bringing the massage head in contact with the skin, with the hand being in contact with the touch piece, so that the human body, the massage head, the touch piece and the power supply are connected to form a closed loop circuit, and a preset electric current flows through the skin; and b. squeezing the material storage container, so that the material body in the material storage container reaches the skin through the material discharging hole on the massage head.

BRIEF DESCRIPTION OF THE DRAWINGS

In order to more clearly illustrate the technical solutions of the embodiments of the present disclosure, brief description is made below on the drawings required to be used in the embodiments. It should be understood that the following drawings only illustrate some of the embodiments of the present disclosure and therefore shall not be regarded as a limitation to the scope, and for a person of ordinary skills in the art, other related drawings also may be obtained from these drawings without inventive effort.

Reference signs: 100-inductive therapeutical instrument; 110-material storage container; 120-shell; 121-battery; 122-lower support; 1221-support cylinder; 1222-support plate; 1223-first insertion boss; 123-circuit board; 124-communicating tube; 125-connector; 1251-annular groove; 1252-position-limiting groove; 126-upper support; 127-touch piece; 130-massage head; 131-vibration motor; 132-motor support; 1321-receiving groove; 1322-fluid channel; 1323-first insertion groove; 1324-second insertion boss; 133-inner plug; 1331-insertion portion; 1332-position-limiting block; 1333-flow guiding portion; 134-outer cover; 1341-cylinder body; 1342-sealing plate; 1342-outer plug; 135-massage surface; 1351-material discharging hole; 136-annular clamping sheet; and 1361-position-limiting protrusion.

DETAILED DESCRIPTION OF THE INVENTION

An object of the present disclosure is to provide an inductive therapeutical instrument generating electric current capable of implementing effective skin care.

Another object of the present disclosure is to provide a skin care method, using the aforementioned inductive therapeutical instrument generating electric current and capable of implementing effective skin care.

In order to make the objects, technical solutions and advantages of the embodiments of the present disclosure clearer, the technical solutions of the embodiments of the present disclosure will be described clearly and completely below with reference to the drawings of the embodiments of the present disclosure. Apparently, the embodiments described are some of the embodiments of the present disclosure, rather than all of the embodiments. All the other embodiments that are obtained by a person of ordinary skills in the art without inventive effort on the basis of the embodiments of the present disclosure shall be covered by the protection scope of the present disclosure.

Thus, the following detailed description of the embodiments of the present disclosure provided in the drawings is not intended to limit the scope of the present disclosure claimed, but is merely representative of the selected embodiments of the present disclosure. All the other embodiments that are obtained by a person of ordinary skills in the art without inventive effort on the basis of the embodiments of the present disclosure shall be covered by the protection scope of the present disclosure.

In the description of the present disclosure, it should be understood that the terms denoting the orientation or positional relationship are based on the orientation or positional relationship indicated by the drawings, which only serve to facilitate describing the present disclosure and simplify the description, rather than indicating or implying that the device or element referred to must have a particular orientation, or is constructed or operated in a particular orientation, and therefore cannot be construed as a limitation on the present disclosure.

In the present disclosure, unless otherwise explicitly specified or defined, the terms such as "install", "link", "connect" and "fix" shall be understood in broad sense, which may, for example, refer to fixed connection, detachable connection or integral connection; may refer to mechanical connection or electrical connection; may refer to direct linking or indirect linking by means of an intermediate medium; and may refer to internal communication between two elements, or interaction relationship between two elements. A person of ordinary skills in the art could understand the specific meaning of the above terms in the present disclosure according to specific situations.

In the description of the present disclosure, it should be noted that the orientation or positional relationship denoted by the terms such as "center", "upper", "lower", "left", "right", "vertical", "horizontal", "inner" and "outer" is based on the orientation or positional relationship indicated by the drawings, or refers to the orientation or positional relationship where the product of the present disclosure is normally placed when in use, which only serves to facilitate describing the present disclosure and simplify the description, rather than indicating or implying that the device or element referred to must have a particular orientation, or is constructed or operated in a particular orientation, and therefore cannot be construed as a limitation on the present disclosure. In addition, the terms such as "first" and "second" are only used for differentiated description and cannot be understood as an indication or implication of relative importance.

In addition, the terms such as "horizontal", "vertical" and "pendulous" do not necessarily require that the components must be absolutely horizontal or pendulous, rather, they can be slightly inclined. For example, the term "horizontal" merely refers to a more horizontal direction relative to the direction indicated by the term "vertical", and does not necessarily require that the structure must be absolutely horizontal, rather, it can be slightly inclined.

In the present disclosure, unless otherwise explicitly specified or defined, the first feature being "on" or "under" the second feature may include the first feature and the second feature being in direct contact, or the first feature and the second feature being not in direct contact, but in contact with each other through another feature therebetween. Also, the first feature being "on", "above" or "over" the second feature includes the first feature being right above or not right above the second feature, or merely means the level of the first feature being higher than that of the second feature. The first feature being "under", "below" or "beneath" the second feature includes the first feature being directly below or not directly below the second feature, or merely means the level of the first feature being lower than that of the second feature.

Figure 1:
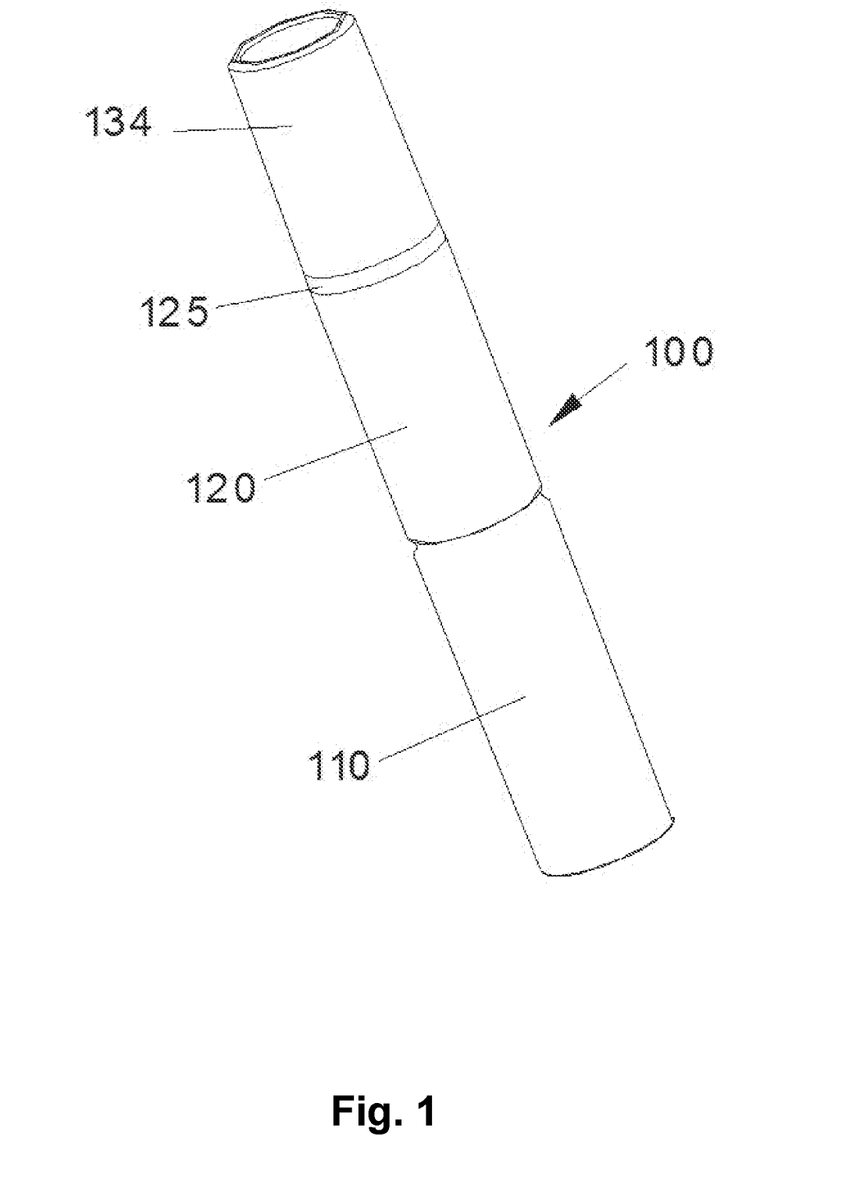
FIG. 1 is a schematic view of external structure of an inductive therapeutical instrument generating electric current according to an embodiment of the present disclosure.
Figure 2:
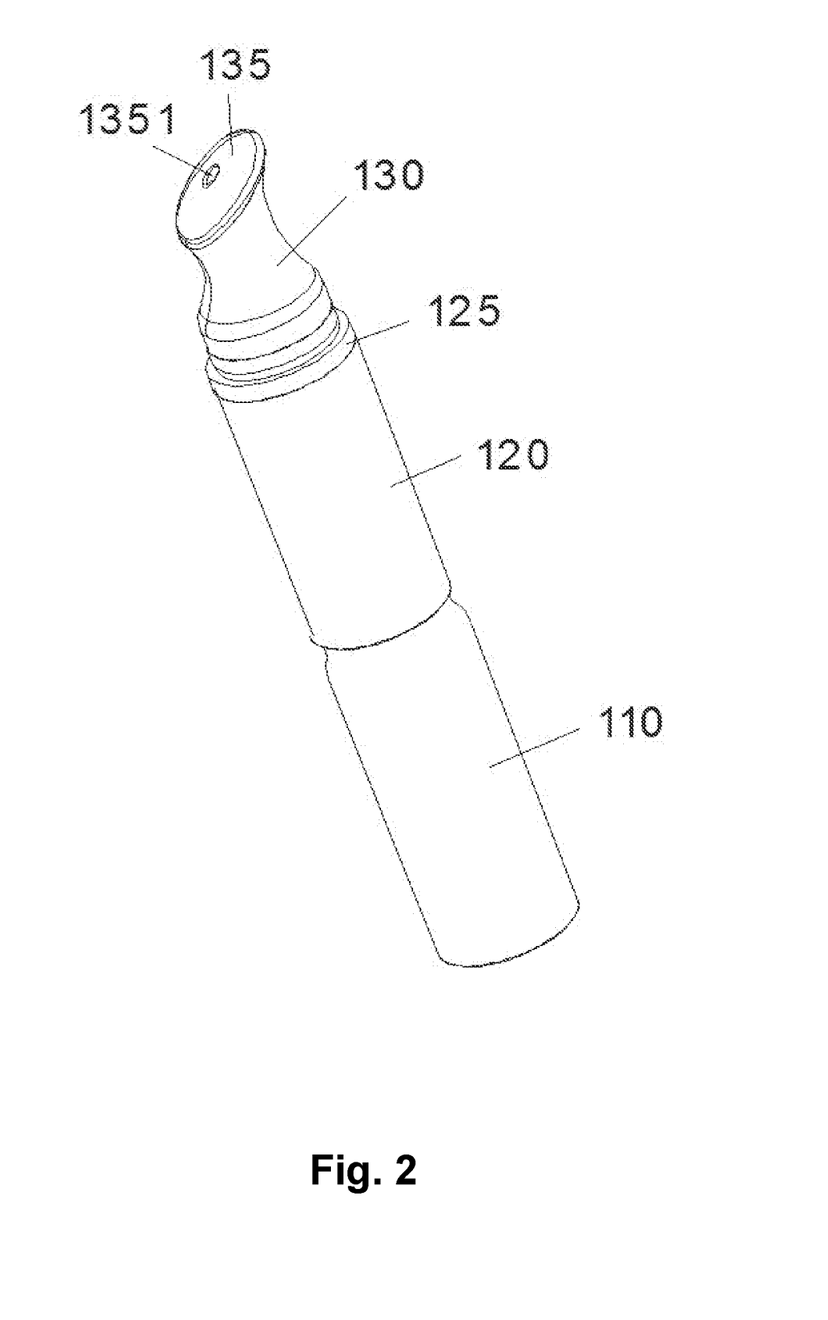
FIG. 2 is a schematic three-dimensional structural view of the inductive therapeutical instrument of FIG. 1 with an outer cover removed.
Figure 3:
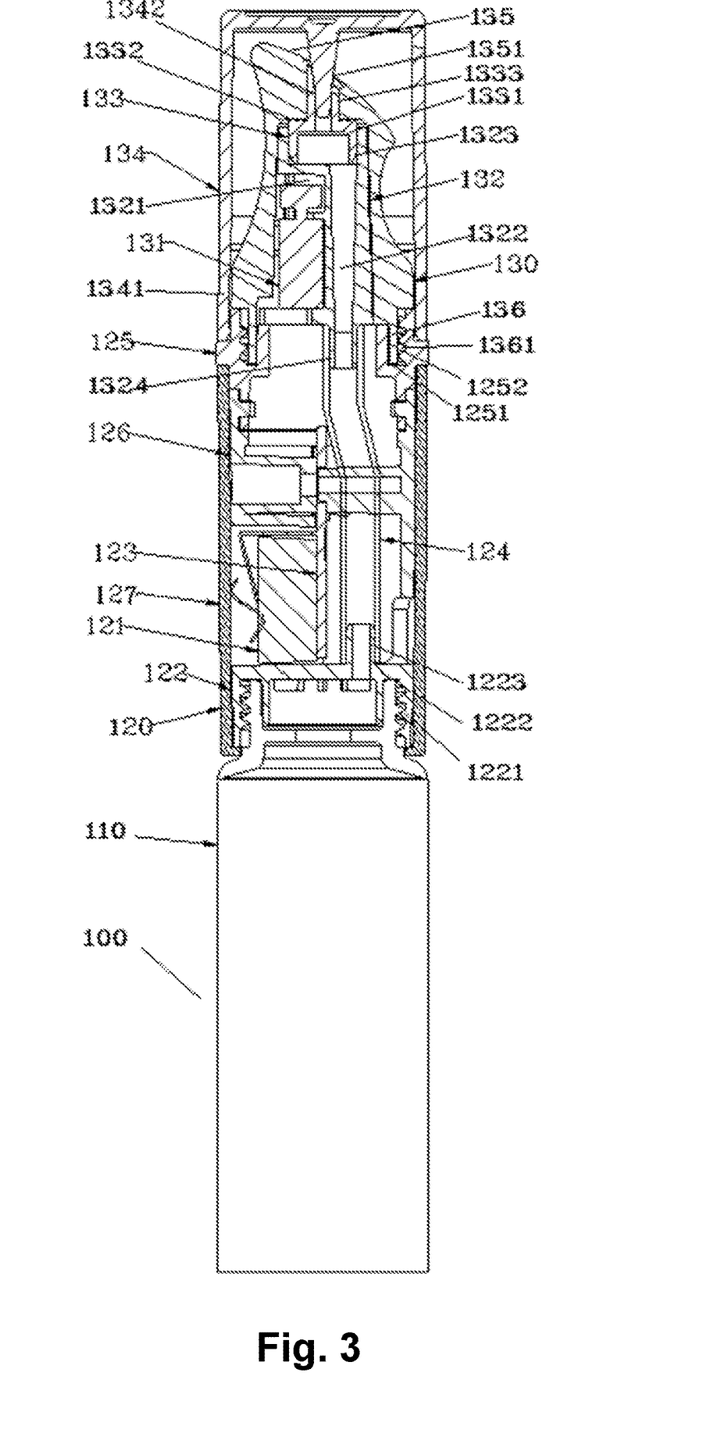
FIG. 3 is a sectional view of the inductive therapeutical instrument generating electric current according to an embodiment of the present disclosure.
Figure 4:
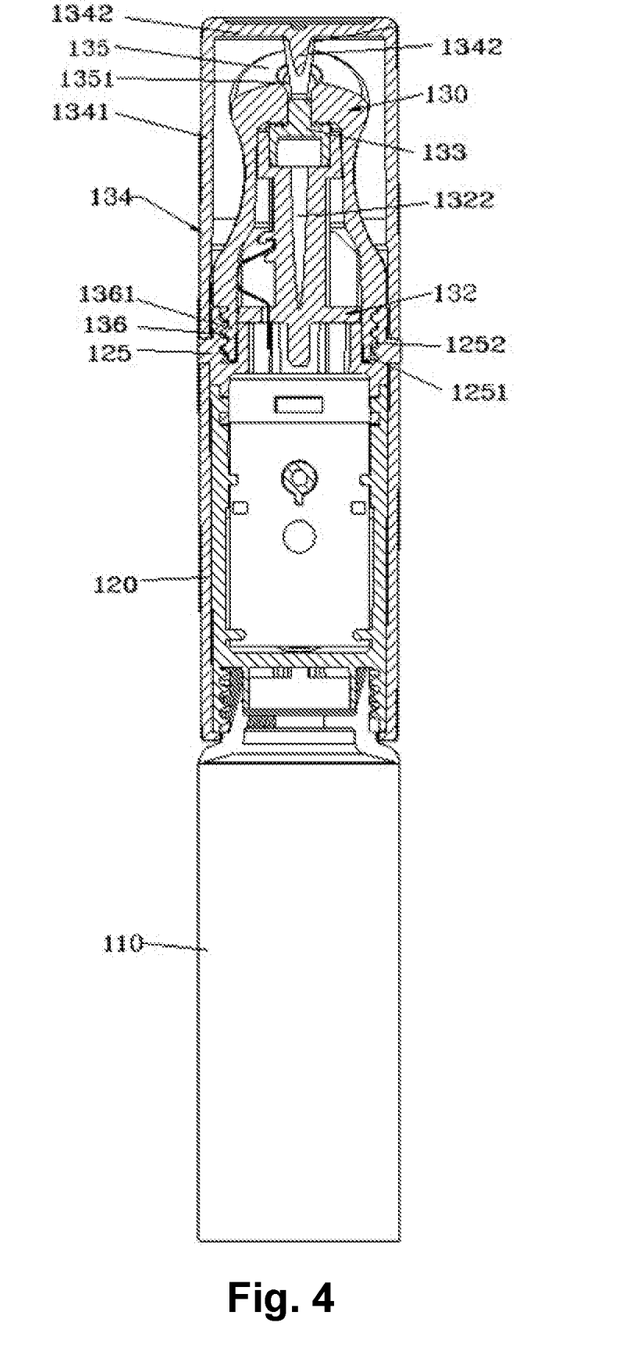
FIG. 4 is a sectional view of the inductive therapeutical instrument generating electric current according to an embodiment of the present disclosure, at another angle.

Referring to FIGS. 1-3, FIG. 1 is a schematic view of external structure of an inductive therapeutical instrument mounted with an outer cover, FIG. 2 is a schematic three-dimensional structural view of the inductive therapeutical instrument without the outer cover, and FIG. 3 is a sectional view of the inductive therapeutical instrument generating electric current 100. The inductive therapeutical instrument generating electric current 100 is mainly used for applying a material body (a skin care product) to the skin and massaging and maintaining the skin. The inductive therapeutical instrument 100 mainly comprises a material storage container 110 and a massage head 130. A material body is stored in the material storage container 110, and the material body is squeezed into the massage head 130 by squeezing the material storage container 110, and is applied to the skin through a material discharging hole 1351 on the massage head 130. Moreover, during use, the inductive therapeutical instrument 100 can generate a microcurrent that acts on the skin so as to improve the skin condition. Specifically, referring to FIGS. 3 and 4, FIG. 4 is a sectional view of the inductive therapeutical instrument generating electric current 100, at another angle. The material storage container 110 may be a cylindrical structure made of a flexible material, with one end closed and the other end provided with a connection hole. The end provided with the connection hole is connected to the massage head 130. When the material storage container 110 is squeezed, the material body therein can be squeezed out through the connection hole. The material body passes through the massage head 130, and then is squeezed out through the material discharging hole 1351 on the massage surface 135 and applied to the skin. It should be noted that the material storage container 110 is not limited to a cylindrical structure, but may be a structure having other shapes.

With continuous reference to FIGS. 3 and 4, the inductive therapeutical instrument 100 further comprises a shell 120, the shell 120 comprises a feeding end and a discharging end, the feeding end is connected to the connection hole on the material storage container 110, and the discharging end is connected to the massage head 130. First, the inner cavity of the shell serves as a receiving cavity for mounting the components such as a power supply and a controller; and second, the inner cavity of the shell 120 is in communication with the inner cavity of the massage head 130, so that the material body squeezed out from the material storage container 110 can pass through the shell 120 and enter the massage head 130, and then is applied to the skin through the material discharging hole on the massage head 130.

Specifically, the shell 120 may be a cylindrical structure convenient for gripping, the two ends of the shell 120 in a length direction are the feeding end and the discharging end, respectively, and the feeding end of the shell 120 is provided with a lower support 122, and a battery 121 and a controller are both disposed on the lower support 122. Specifically, a circuit board 123 may be provided on the lower support, and the controller is assembled on the circuit board 123. In order to fix the battery 121 and circuit board 123, the feeding end of the shell 120 is provided with the lower support 122, the lower support 122 may be a cylindrical structure as a whole, comprising a support cylinder 1221 and a support plate 1222, the support plate is provided at the top end of the support cylinder, and the support plate 1222 is provided thereon with a through hole configured to allow the material body to pass through. The support cylinder 1221 is connected to the feeding end of the shell 120 in a clamping manner, and the support cylinder 1221 is in threaded connection with the material storage container 110. A communicating tube 124 is connected to the through hole on the support plate 1222, and the other end of the communicating tube 124 is connected to the massage head 130. When the material storage container 110 is squeezed, the material body in the material storage container 110 is squeezed upwardly to the feeding end of the shell, and enters the communicating tube 124 through the through hole on the support plate 1222, and then enters the massage head 130 through the top end of the communicating tube 124, and finally is squeezed out through the material discharging hole 1351 on the massage surface 135. Specifically, the outer diameter of the shell 120 may be 19 mm-30 mm, and the vibration motor may be an eccentric vibration motor or a button-type vibration motor.

Specifically, the circuit board 123 may further be provided thereon with a rheostat for adjusting the resistance, so as to facilitate the adjustment of the magnitude of the electric current of the inductive therapeutical instrument.

The circuit board 123 is mounted on the support plate, and the circuit board 123 comprises a controller that is electrically connected to a power supply. A touch piece capable of conducting electricity is provided on an outer wall of the shell 120, and the touch piece is electrically connected to the power supply.

The discharging end of the shell 120 is provided with a connector 125 configured to be connected to the massage head 130. The connector 125 is of a cylindrical structure as a whole, and the connector 125 is connected to the discharging end of the shell 120 in a clamping manner. Moreover, the connector 125 is provided thereon with an annular groove 1251, and the massage head 130 is provided thereon with an annular clamping sheet 136 and is clamped in the annular groove 1251 by the annular clamping sheet 136. Here illustrated is a specific form in which the connector 125 is connected to the massage head 130. In assembly, it is merely required that the annular clamping sheet 136 at the bottom end of the massage head 130 is aligned with the annular groove 1251 on the connector 125 and inserted into the same forcibly.

In this embodiment, a position-limiting groove 1252 may be provided on the side wall of the annular groove 1251 in the circumferential direction thereof, a position-limiting protrusion 1361 is provided on the side wall of the annular clamping sheet 136 in the circumferential direction thereof, and the position-limiting protrusion 1361 is matched with the position-limiting groove 1252. At the time of assembling the connector 125 and the massage head 130, the annular clamping sheet 136 is first aligned with and inserted into the annular groove 1251, the annular groove 1251 guides the insertion path of the annular clamping sheet 136, and during the insertion, the annular groove 1251 is pressed by the outwardly protruding position-limiting protrusion 1361 on the annular clamping sheet 136, until the position-limiting protrusion 1361 is caught in the position-limiting groove 1252 of the annular groove 1251 to complete the assembly. The position-limiting groove 1252 limits the position of the position-limiting protrusion 1361 to lock the annular clamping sheet 136 and the massage head 130 on the connector 125.

As shown in FIGS. 3 and 4, the massage head 130 is a hollow structure made of an aluminum alloy material. The massage head 130 comprises the massage surface provided thereon with the material discharging hole 1351; and the massage head 130 is connected to the material storage container 110, and the material body can flow through the interior of the massage head 130 and flow out from the material discharging hole. In other embodiments, the massage head 130 may be made of other electrically conductive materials.

Specifically, the massage head 130 has a hollow structure, a motor support 132 is mounted inside the massage head 130, a receiving groove 1321 is provided on a side portion of the motor support, and a vibration motor 131 is mounted in the receiving groove 1321. For the arrangement of the motor support 132, on the one hand, the motor support can be used as a base to increase the mounting firmness of the vibration motor 131 inside the massage head 130; and on the other hand, the receiving groove 1321 on the side portion of the motor support 132 can also protect the vibration motor. The motor support 132 is provided thereon with a fluid channel 1322 having one end connected to the communicating tube 124, and the other end provided with an inner plug 133. The inner plug 133 is provided thereon with a through hole communicating with the material discharging hole 1351 and used for outflowing of the material body.

In this embodiment, the support plate 1222 of the lower support 122 has a first insertion boss 1223 protruding upwardly in the circumferential direction of the through hole, the lower end of the motor support 132 has a second insertion boss 1324 protruding downwardly in the circumferential direction of the fluid channel 1322, the second insertion boss 1324 is inserted into the top end of the communicating tube 124, and the first insertion boss 1324 is inserted into the bottom end of the communicating tube 124. Here illustrated is a specific form in which the lower support 122, the motor support 132 and the communicating tube 124 are connected. In mounting, the mounting of the communicating tube 124 can be completed just by sleeving the top end of the communicating tube 124 onto the second insertion boss 1324 on the motor support 132 and sleeving the bottom end thereof onto the first insertion boss 1223 of the lower support 122. The mounting and disassembly are both convenient and fast, and the sealing performance of connection is relatively high.

Specifically, in this embodiment, the top end of the motor support 132 may be provided with a first insertion groove 1323, the inner plug 133 is internally hollow and sequentially comprises, from bottom to top, an insertion portion 1331 and a flow guiding portion 1333. The insertion portion 1331 is inserted into the first insertion groove 1323 and in communication with the fluid channel 1322, and the top end of the flow guiding portion 133 is inserted into the material discharging hole 1351. Here illustrated is a specific form in which the inner plug 133 is connected to the motor support 132. During assembly, the insertion portion 1331 of the inner plug 133 is aligned with and inserted into the first insertion groove 1323 of the motor support 132, the top end of the flow guiding portion 1331 of the inner plug 133 is inserted into the material discharging hole 1351 of the massage surface 135, and the cavity of the inner plug 133 is in communication with the fluid channel 1322 of the motor support 132. When the material storage container 110 is squeezed, the feed liquid sequentially passes through the lower support 122 into the communicating tube 124, enters the fluid channel 1322 of the motor support 132 through the communicating tube 124, enters the inner cavity of the inner plug 133, and is squeezed out from the material discharging hole 1351.

In this embodiment, the top portion of the insertion portion 1331 is provided with a position-limiting block 1332 in the circumferential direction thereof, and the top end of the motor support 132 abuts against the position-limiting block 1332. The position-limiting block 1332 protrudes outwardly in all sides and has a size larger than the first insertion groove 1323. The insertion portion 1331 of the inner plug 133 is inserted into the first insertion groove 1323. The position-limiting block 1332 limits the insertion depth of the insertion portion 1331, so as to reduce the occurrence of the case where the flow guiding portion 1333 cannot be cooperated and connected with the material discharging hole 1351 due to excessive insertion of the inner plug 133. In addition, the position-limiting block 1332 enables the joint surface between the inner plug 133 and the motor support 132 to have a break-angle shape, thereby improving the sealing performance of the connection between the inner plug and the motor support and reducing the occurrence of material body overflowing through a gap at the joint.

Moreover, as shown in FIGS. 2-4, the massage head 130 adopts a chamfer design, which closely adheres to the skin and lifts and massages the skin without dead corners in all directions.

The massage head 130 is further provided thereon with a transparent outer cover 134. The outer cover 134 may comprise a cylinder body 1341 and a sealing plate 1342, the sealing plate 1342 disposed at one end of the cylinder body 1341. The outer cover 134 covers the massage head 130. A conical outer plug 1342 is further provided within the cylinder body 1341, and the big end of the outer plug 1342 is connected to the sealing plate 1342. When the outer cover 134 covers the massage head 130, the lower end of the outer plug 1342 is inserted into the through hole of the inner plug 133 to block the through hole, thereby reducing the outflowing of the material body.

In this embodiment, as shown in FIGS. 3 and 4, the shell 120 and the massage head 130 are connected by the connector 125, an annular second insertion groove is provided on an outer side wall of the connector 125, the outer cover 134 covers the massage head 130, the bottom end of the outer cover 134 is inserted into the second insertion groove, and the outer cover 134 matches with the outer surface of the shell 120. After use of the inductive therapeutical instrument, the outer cover is placed on the massage head 130, and cooperation of the second insertion groove and the outer cover not only can realize the clamping connection between the outer cover and the connector, but also can limit the mounting position of the outer cover and ensure the protective effect of the outer cover on the massage head. In addition, the outer cover matches with the outer surface of the shell, and the inductive therapeutical instrument is a smooth column as a whole, enabling higher integrity.

The working principle of the inductive therapeutical instrument generating electric current 100 provided in this embodiment is as follows:

Before use, the material body is stored in the material storage container 110; and when in use, the massage surface (made of electrically conductive material) of the massage head 130 is placed on the skin, the material storage container 110 is squeezed so that the material body enters the fluid channel 1322 of the motor support 132 in the massage head 130 through the communicating tube 124, then passes through the inner plug 133 and finally reaches the skin through the material discharging hole 1351 on the massage head 130. When microcurrent maintenance is required, the touch piece is held by hand, so that the battery 121, the massage head 130, the human body (equivalent to an electrically conductive element) and the touch piece are connected in series to form a closed loop circuit, thereby generating a microcurrent.

Experiments have shown that microcurrent has many benefits to the human body:

promoting vasodilation to relax vascular smooth muscle, accelerating blood circulation, promoting blood circulation and removing blood stasis, and being capable of correcting ischemia and anoxia, and improving microcirculation; and promoting subsiding of the tissue inflammation, thereby eliminating the swelling to relieve pain; and promoting cell metabolism, accelerating the discharge of wastes from cells, and balancing endocrine disorders; decreasing the excitability of nerve endings, and significantly improving the pain threshold; improving blood lipid metabolism, reducing cholesterol synthesis to make it difficult for cholesterol to deposit on blood vessel walls; balancing blood pressure, improving cardiovascular and cerebrovascular metabolism and myocardial ischemia, improving the oxygen carrying capacity of erythrocytes, to reduce erythrocyte aggregation and improve blood viscosity; improving the immune function of the human body, and having anti-tumor effect; eliminating the free radicals in the body, strengthening the anti-oxidation ability of the cells, protecting the integrity of the cell membranes, and having anti-aging effect on the human body; and eliminating fatigue, enhancing physical strength and improving human body function.

Specifically, the model number of the vibration motor used in the present disclosure may be 0408, the maximum power thereof is 0.072 W, the maximum current that the vibration motor can withstand is 45 mA, and the battery voltage is 1.6 V. When the vibration motor is in normal operation, the current in the whole closed loop circuit is 0.02 mA, that is, the current passing through the human body is about 0.02 mA, and the probability of the above current causing damages to the human body can be ignored.

In addition, in this embodiment, the power supply may be a button battery, or a rechargeable device such as a rechargeable battery or the like; alternatively, the power supply may also be an element configured to be connected to an external power supply.

The present embodiment provides a skin care method, using the inductive therapeutical instrument generating electric current 100 described above and comprising the steps of:

a. hand-holding the inductive therapeutical instrument generating electric current 100, and bringing the massage head 130 in contact with the skin, with the hand being in contact with the touch piece, so that the human body, the massage head 130, the touch piece and the power supply are connected to form a closed loop circuit, and a preset electric current flows through the skin; and b. squeezing the material storage container, so that the material body in the material storage container reaches the skin through the material discharging hole on the massage head 130.

By adjusting the resistance on the circuit board 123, the magnitude of the electric current can be adjusted.

The advantageous effects of the present disclosure include at least the following:

For the inductive therapeutical instrument generating electric current obtained by the above-described design in the present disclosure, when in use, a material body (i.e., a skin care product) is first put into the material storage container, then the inductive therapeutical instrument is held by hand with the hand pressing the touch piece, and the massage head is put on the skin, such that the human body, the massage head, the touch piece and the power supply are connected to form a closed loop circuit, and a microcurrent flows through the skin; and by squeezing the material storage container, the material body enters the massage head from the material storage container and is finally squeezed onto the skin through the material discharging hole.

Since the inductive therapeutical instrument can generate a microcurrent and massage the skin, the above inductive therapeutical instrument can promote vasodilation to relax vascular smooth muscle, accelerate blood circulation, promote blood circulation and remove blood stasis, and can correct ischemia and anoxia, and improve microcirculation.

In the skin care method obtained by the above-described design in the present disclosure, the above inductive therapeutical instrument generating electric current is used, which can massage the skin while applying a skin care product to the skin, and improve the skin condition by the action of the microcurrent.

The descriptions above are only preferred embodiments of the present disclosure, which are not used to limit the present disclosure. For a person skilled in the art, the present disclosure may have various modifications and variations. Any modifications, equivalent substitutions, improvements etc. within the spirit and principle of the present disclosure shall all be included in the scope of protection of the present disclosure.

INDUSTRIAL APPLICABILITY

The inductive therapeutical instrument generating electric current and the skin care method provided in this embodiment are capable of generating a microcurrent and massaging the skin, which can promote vasodilation of the user to relax vascular smooth muscle, accelerate blood circulation, promote blood circulation and remove blood stasis, and can correct ischemia and anoxia, and improve microcirculation.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

The invention claimed is:

1. An inductive therapeutical instrument generating electric current, comprising:

a material storage container, configured to store a material body, the material storage container being compressible;

a massage head, which is of a hollow structure and made of an electrically conductive material, the massage head comprising a massage surface provided thereon with a material discharging hole; the massage head being connected with the material storage container, and the material body capable of flowing through an interior of the massage head and flowing out from the material discharging hole;

a vibration motor, provided in the massage head; and a touch piece and a power supply, the touch piece being made of a second electrically conductive material, the touch piece, the vibration motor and the massage head being connected in series, and the massage head, the touch piece and the power supply being connectable by an electrically conductive element to form a closed loop circuit; and a shell comprising a feeding end and a discharging end, the feeding end being connected to the material storage container, and the discharging end being connected to the massage head;

wherein, the power supply is a battery and is disposed in the shell, and a controller disposed in the shell, wherein the controller is electrically connected to the power supply and is configured to control the closed loop circuit to generate a microcurrent;

the shell is of a cylindrical structure, and wherein two ends of the shell in a length direction are respectively the feeding end and the discharging end, the feeding end of the shell is provided with a lower support, and the battery and the controller are both disposed on the lower support;

a circuit board is provided on the lower support, wherein the controller is assembled on the circuit board, and the circuit board is further provided thereon with a rheostat capable of adjusting a resistance and configured to adjust a magnitude of an electric current of the inductive therapeutical instrument;

the lower support comprises a support cylinder and a support plate provided at a top end of the support cylinder, the circuit board and the battery are both disposed on the support plate; and the support plate is provided thereon with a through hole allowing a feed liquid to flow through;

the feeding end of the shell is sleeved outside the support cylinder, with an opening facing downwardly, and the material storage container is inserted in the support cylinder and is in threaded connection with the support cylinder;

a motor support is disposed in the massage head, a receiving groove is provided on a side portion of the motor support, and the vibration motor is mounted in the receiving groove;

the motor support is provided thereon with a fluid channel, an outlet of the fluid channel is in communication with the material discharging hole and an inlet of the fluid channel is in communication with the discharging end of the shell;

a communicating tube is provided in the shell, with one end communicating with the fluid channel and the other end communicating with the material storage container; and the support plate of the lower support has a first insertion boss protruding upwardly in a circumferential direction of the through hole, a lower end of the motor support has a second insertion boss protruding downwardly in a circumferential direction of the fluid channel, the second insertion boss is inserted into a top end of the communicating tube, and the first insertion boss is inserted into a bottom end of the communicating tube.

2. The inductive therapeutical instrument generating electric current according to claim 1, wherein the battery is a button battery or a rechargeable device.

3. The inductive therapeutical instrument generating electric current according to claim 1, wherein the discharging end of the shell is provided with a connector provided thereon with an annular groove; and the massage head is provided thereon with an annular clamping sheet that is clamped in the annular groove.

4. The inductive therapeutical instrument generating electric current according to claim 3, wherein a position-limiting groove is provided on a side wall of the annular groove in a circumferential direction thereof, a position-limiting protrusion is provided on a side wall of the annular clamping sheet in a circumferential direction thereof, and the position-limiting protrusion is matched with the position-limiting groove.

5. The inductive therapeutical instrument generating electric current according to claim 1, further comprising an inner plug, the inner plug having a cylindrical structure, with one end communicating with the fluid channel of the motor support and the other end inserted into the material discharging hole.

6. The inductive therapeutical instrument generating electric current according to claim 5, wherein a top end of the motor support is provided with a first insertion groove, the inner plug is internally hollow and sequentially comprises, from bottom to top, an insertion portion and a flow guiding portion, the insertion portion is inserted into the first insertion groove and is in communication with the fluid channel, and a top end of the flow guiding portion is inserted into the material discharging hole.

7. The inductive therapeutical instrument generating electric current according to claim 6, wherein a top portion of the insertion portion is provided with a position-limiting block in a circumferential direction thereof, and the top end of the motor support abuts against the position-limiting block.

8. The inductive therapeutical instrument generating electric current according to claim 5, further comprising an outer cover, the outer cover comprising a cylinder body and a sealing plate disposed at a top end of the cylinder body; and the outer cover covering the massage head.

9. The inductive therapeutical instrument generating electric current according to claim 8, wherein a conical outer plug is provided in the cylinder body, with a big end connected to the sealing plate and a small end movably inserted into the inner plug.

10. The inductive therapeutical instrument generating electric current according to claim 8, wherein the shell and the massage head are connected by a connector, an annular second insertion groove is provided on an outer side wall of the connector, the outer cover covers the massage head, a bottom end of the outer cover is inserted into the second insertion groove, and the outer cover matches with an outer surface of the shell.

11. The inductive therapeutical instrument generating electric current according to claim 1, wherein an outer diameter of the shell is 19 mm-30 mm.

12. A skin care method, using the inductive therapeutical instrument generating electric current according to claim 1, comprising steps of:

a. hand-holding the inductive therapeutical instrument generating electric current, and bringing the massage head in contact with a skin, with a hand being in contact with the touch piece, so that a human body, the massage head, the touch piece and the power supply are connected to form a closed loop circuit, and a preset electric current flows through the skin; and b. squeezing the material storage container, so that the material body in the material storage container reaches the skin through the material discharging hole on the massage head.

* * * * *